US007120501B2

(12) United States Patent
Boylston et al.

(10) Patent No.: US 7,120,501 B2
(45) Date of Patent: Oct. 10, 2006

(54) TRANSCANAL COCHLEAR IMPLANT SYSTEM

(75) Inventors: Byron Lee Boylston, Holden Beach, NC (US); Manning Miles Goldsmith, Savannah, GA (US)

(73) Assignee: Microphonics, Inc., Plano, TX (US)

( * ) Notice: Subject to any disclaimer, the term of this patent is extended or adjusted under 35 U.S.C. 154(b) by 482 days.

(21) Appl. No.: 10/636,084

(22) Filed: Aug. 6, 2003

(65) Prior Publication Data

US 2004/0093040 A1    May 13, 2004

Related U.S. Application Data

(63) Continuation-in-part of application No. 10/054,092, filed on Jan. 22, 2002, now Pat. No. 6,671,559.

(60) Provisional application No. 60/263,600, filed on Jan. 23, 2001.

(51) Int. Cl.
*A61N 1/18* (2006.01)
(52) U.S. Cl. .................................................. 607/57
(58) Field of Classification Search ............ 606/55–56; 623/10; 607/55–56, 57; 381/312, 328
See application file for complete search history.

(56) References Cited

U.S. PATENT DOCUMENTS

| 3,751,605 | A | * | 8/1973 | Michelson ............... 607/57 |
| 4,689,819 | A | * | 8/1987 | Killion .................... 381/321 |
| 5,120,953 | A | | 6/1992 | Harris |
| 5,383,467 | A | | 1/1995 | Auer et al. |
| 6,185,271 | B1 | | 2/2001 | Kinsinger |
| 6,231,604 | B1 | * | 5/2001 | von Ilberg ............... 623/10 |

OTHER PUBLICATIONS

Berlinger et al., "Tinnitus Suppression in Cochlear Implantation," pp. 118-130.
Edgerton et al., "The Effects of Signal Processing by the House-Urban Single-Channel Stimulator on Auditory Perception Abilities of Patients with Cochlear Implants," Annals New York Academy of Sciences, House Ear Institute, 1983, pp. 311-322.
Fretz et al., "Design and Function: A Physical and Electrical Description of the 3M HOuse Cochlear Implant System," Ear and Hearing, vol. 6, No. 3 Supp., 3M Company, St. Paul, MI, 1985, pp. 14S-19S.
Fravel, "Cochlear Implant Electronics Made Simple," Otolaryngologic Clinics North America, vol. 19, No. 2, 3M Company, St. Paul, MI, May 1986, pp. xi-xxii.
House, 37 Cochlear Implants: Two Monographs (and two papers by David House), Allhear@Allhear.com, 1999.

* cited by examiner

*Primary Examiner*—Mark Bockelman
(74) *Attorney, Agent, or Firm*—Jason A. Bernstein; Charles L. Warner II; Powell Goldstein LLP (57) ABSTRACT

A magnetic field modulation system for a cochlear implant: The magnetic field modulation system receives audible tones and processes the tones into radio frequency signals that are received by a radio frequency coil system. The radio frequency coil system has a transmitting coil and a receiving coil wound in a plurality of configurations. The transmitting coil is implanted in the ear canal wherein it receives processed radio frequency signals. The receiving coil is implanted into the middle ear wherein it receives the radio frequency signals from the transmitting coil. The receiving coil is hermetically sealed inside an enclosure wherein it receives and demodulates the radio frequency signal. Audio electrical signals are extracted from the demodulated radio frequency signal and delivered to the cochlea via an electrode. The audio electrical signals are received by the human brain via the nerves from the cochlea.

25 Claims, 5 Drawing Sheets

TRANSCANAL COCHLEAR IMPLANT SYSTEM

CROSS-REFERENCE TO RELATED APPLICATIONS

This application is a continuation-in-part of application No. 10/054,092, filed Jan. 22, 2002, entitled TRANSCANAL, TRANSTYMPANIC COCHLEAR IMPLANT SYSTEM now U.S. Pat No. 6,671,559, and provisional patent application 60/263,600, filed Jan. 23, 2001 both commonly assigned to the assignee of the present application, the disclosures of which is incorporated by reference in their entirety herein.

FIELD OF THE INVENTION

The present invention is directed to the field of transcanal cochlear implants for patients with hearing impairment and/or tinnitus. More particularly, it is a magnetic field modulation system for a transcanal cochlear implant that requires a minimum of surgical intrusion and may be performed at a physician's office under local anesthesia.

BACKGROUND

A transcanal cochlear implant is ideally suited for the profoundly deaf where conventional amplifying hearing aids are of limited or no value. That is to say, with maximum gain delivered by the most powerful hearing aids, these profoundly deaf individuals cannot hear sound and hence cannot discriminate and understand speech. In addition, an estimated 200–300 million people have various patterns of severe sensorineural hearing loss, which are imperfectly rehabilitated via hearing aids. An example of such is the so called "ski-sloped hearing loss," where there is near normal hearing in the low to middle frequency range, but the hearing drops out dramatically in the higher frequencies. For these types of hearing loss, amplification is ineffective because the cochlea cannot perform its transductive function of converting the mechanical energy of sound to the electrical current which is ultimately perceived as sound by the brain. The inner ear structures responsible for this transductive function are known as hair cells. The electrical currents which they produce in response to the mechanical stimulation by sound are known as cochlear microphonics. When these hair cells are sufficiently damaged as in the above mentioned scenarios no amount of amplification will be effective.

The cochlear implant is, in effect, a bionic ear in that it replaces the lost cochlear microphonic with an electrical current that is the precise analog of sound. Currently, United States Food and Drug Administration ("FDA") has approved cochlear implants. The approved cochlear implant are so-called multichannel long electrode devices. They are expensive, highly complex devices that must be surgically introduced via a complicated and (for the average otolaryngologist) risky procedure under general anesthesia known as the facial recess mastoidectomy. The estimated cost of these cochlear implant systems, including surgery, anesthesia, hospital and programming fees is currently quite high. The hardware necessary to program these devices adds further to the high cost. The time to program the first map for these devices averages from four to twelve hours depending upon the age of the patient and other factors. The prohibitive price and impractical complexity deter accessibility to the vast majority of the global deaf population. Furthermore, the average otologist in the developing countries of the world typically does not have the sophistication, expertise and equipment to confidently undertake the facial recess mastoidectomy in order to introduce the internal component of the multichannel systems.

The most tragic irony of all is that the multichannel long electrode devices can destroy residual hearing when they are inserted into the cochlea. This well acknowledged fact makes these devices difficult to justify in very young infants where the precise degree of hearing loss is often in doubt. Furthermore, the electronics package and receiver coil for such a complex sound-processing scheme would not fit within the middle ear space.

SUMMARY OF THE INVENTION

The present invention is a magnetic field modulation system for a transcanal cochlear implant. The magnetic field modulation system may, if desired, have at least one microphone electrically connected to the input of a digital audio signal processor, which is then electrically connected to the input of a switching class-D type amplifier. The amplifier may, if desired, be a discrete component or integrated with either the digital signal processor, or a transmitting coil. The digital audio signal processor, microphone and switching amplifier receive power from a portable power source. The signal from the microphone is processed by the digital audio signal processor and then is passed on to the switching amplifier. The transmitting coil has a very low inductive reactance enabling it to operate synchronously with the switching frequency of the amplifier. This encodes the audio input signal into a radio frequency (RF) signal of the transmitting coil.

The magnetic field modulation system has an implanted portion that passively demodulates the RF signals that are received from the transmitting coil and requires no connection to the power source. The implanted portion is comprised of a receiving RX coil and a capacitor which are hermetically sealed inside an enclosure. The electrode is flexible and has an electrical insulation coating over its entire length with the exception of the inserted tip of the electrode. It is the tip of the electrode that delivers the audio signal inside the cochlea. The distance that the tip electrode can be inserted into the cochlea is limited by a mechanical stop that engages and helps seal the round window opening of the cochlea after insertion. This mechanical stop is part of an integral supporting structure on the enclosure that extends to the round window of the cochlea. The mechanical stop is installed in the round window by the surgeon to help fix the implants location, control insertion depth of the electrode and help seal the cochlea after insertion.

The receiving coil of the implant portion may, if desired, be configured as an air core coil, dual-lobe coil or a C-shaped coil. The extracted audio signal is delivered to the cochlea via an electrode. The cochlea transmits the electrical audio signal to the human brain.

When taken in conjunction with the accompanying drawings and the appended claims, other features and advantages of the present invention become apparent upon reading the following detailed description of embodiments of the invention.

BRIEF DESCRIPTION OF THE DRAWINGS

The invention is illustrated in the drawings in which like reference characters designate the same or similar parts throughout the figures of which.

DETAILED DESCRIPTION OF THE INVENTION

Figure 1:
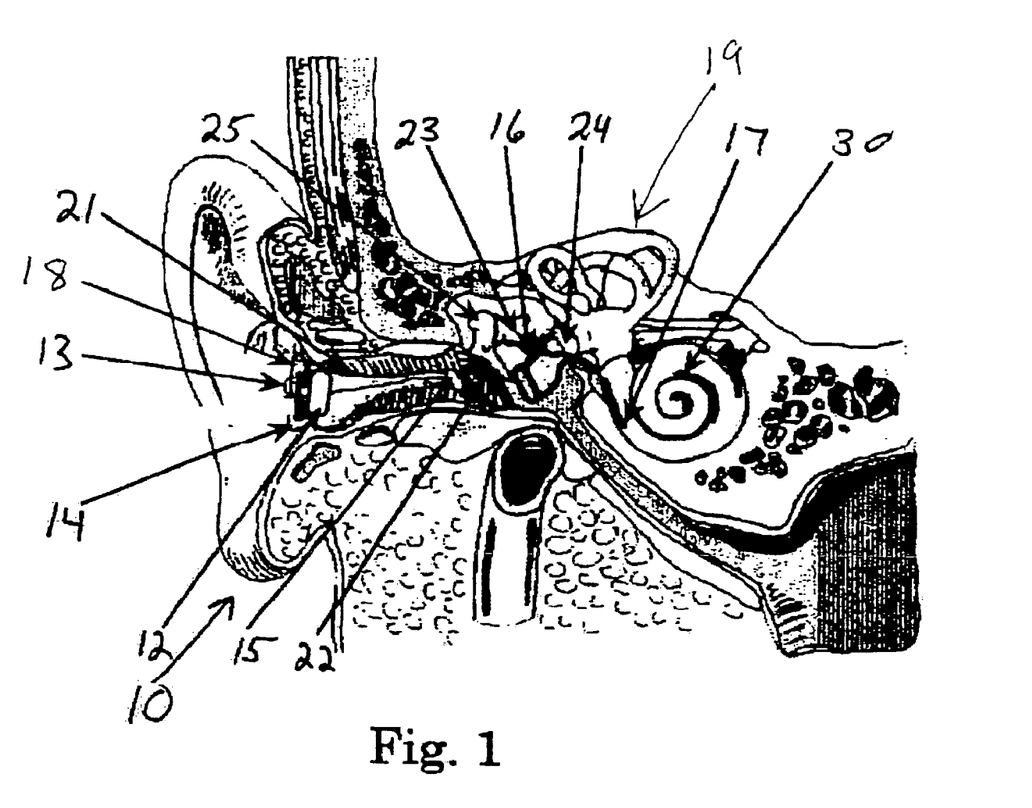
FIG. 1 Illustrates a sectional diagram of a human ear incorporating one exemplary embodiment of the present invention, FIG. 2 Illustrates a top level block diagram of the exemplary embodiment present invention of FIG. 1, FIG. 3 Illustrates a perspective of the transmitting coil of the exemplary embodiment of FIG. 1.

Before describing in detail the exemplary embodiments of the apparatus 10 of present invention, FIG. 1 shows a magnetic field modulation system 18 comprising a synchronously-coupled, radio-frequency (RF) coil system that implements a passive (un-powered) demodulation circuit to produce an audio frequency output signal for a transcanal cochlear implant 19. It should be observed that the invention resides primarily in a novel structural combination of conventional materials and discrete components associated with the aforementioned magnetic field modulation system 18 and not in the particular detailed configuration thereof. Accordingly, the structure and arrangement of these conventional components have, for the most part, been illustrated in the drawings by readily understandable diagram representations and schematic diagrams. The drawings show only those specific details that are pertinent to the apparatus 10 of the present invention in order not to obscure the disclosure with structural details which will be readily apparent to those skilled in the art having the benefit of the description herein. Thus, the schematic diagram illustrations of the Figures do not necessarily represent the mechanical structural arrangement of the exemplary system, and are primarily intended to illustrate major hardware structural components of the apparatus 10 of the present invention in a convenient functional grouping whereby the present invention may be more readily understood.

Figure 2:
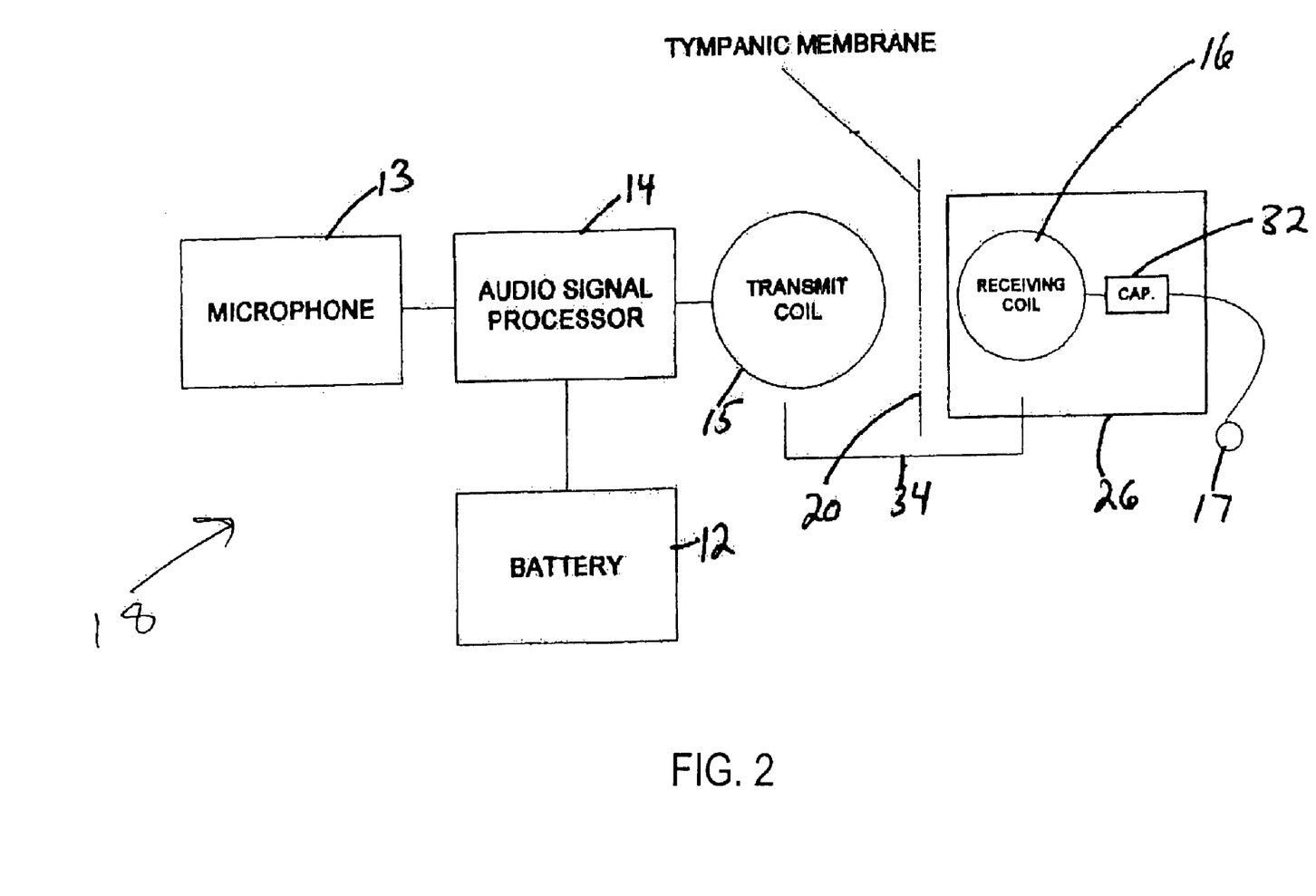

Overview of the present invention: The present invention 10, as shown in FIG. 2, is a magnetic field modulation system 18 for a transcanal cochlear implant 19. The magnetic field modulation system 18 comprises at least one microphone 13 electrically connected to the input of a digital audio signal processor 14 which is then electrically connected to the input of a switching class-D type amplifier. The amplifier may, if desired, be a discrete component or integrated with either the digital signal processor 14 or the transmitting coil 15

Typically, a "Class-D" or "digital switching amplifier" has a very high-frequency output signal that is connected to a highly inductive load. Examples of highly inductive loads are an audio speaker and a hearing aid i.e., the receiver portion of the hearing aid. This highly inductive load acts as an electrical storage device and has the effect of averaging out the amplifier's high switching frequency leaving the original, demodulated and amplified audio frequencies to drive the load. The magnetic field produced by this type of system is limited to the audio spectrum by its high inductive reactance.

The apparatus 10 of the present invention does not implement a standard switching class-D amplifier in this way. Instead of using a highly inductive load, the inductive reactance of the load (transmitting coil 15) is greatly reduced. The inductive reactance is reduced until it no longer averages out the amplifier's high switching frequency, but instead cycles on and off in synchronization with that switching frequency. The frequency of the magnetic field produced in this operating mode is also in-sync with the switching frequency that may, if desired, be about 2-MHz.

In operation: The digital audio signal processor 14, microphone 13 and switching amplifier receive power from a portable power source 12. The signal from microphone 13 is processed by the digital audio signal processor 14 and then passed on to the switching amplifier. The transmitting coil 15 has a very low inductive reactance enabling it to operate synchronously with the switching frequency of the amplifier. This encodes the audio input signal into the RF signal of the transmit coil 16.

The magnetic field modulation system 18 has an implanted portion that passively demodulates the RF signals that are received from the transmitting coil 16 and requires no connection to the power source. The implanted portion is comprised of receiving RX coil 16, capacitor 32 and electrode 17 which are hermetically sealed inside an enclosure 26. The enclosure may be made of any suitable material, such as, but not limited to, polymer, polymer derivative or polymer embedded metal, silver, gold, titanium, anodized metal and the like. The enclosure may if desired, include a sealed feed-through connection to deliver the audio signal to the electrode attached on the outside of the enclosure. The electrode is flexible and has an electrical insulation coating over its entire length with the exception of the inserted tip of the electrode. It is the tip of the electrode that delivers the audio signal inside the cochlea. The distance that the tip electrode can be inserted into the cochlea is limited by a mechanical stop that engages and helps seal the round window opening of the cochlea after insertion. The mechanical stop is part of an integral supporting structure of the enclosure that extends to the round window of the cochlea. The mechanical stop is installed in the round window by the surgeon to help fix the implants location, control insertion depth of the electrode and help seal the cochlea after insertion. The conductive outer surfaces of the sealed enclosure and any conductive supporting structure that attached to the enclosure combine to provide the electrical signal return path. The extracted audio signal is delivered to the cochlea via the electrode 17. The electrical signals are received by the human brain via the nerves from the cochlea.

The magnetic field modulation system 18, in concert with the apparatus 10 of the present invention, may best be understood by first reviewing the mechanics of the human ear and how it functions to transfer sounds to the brain. The human ear consists of an auditory canal terminating externally in a pinna and internally at the ear drum or tympanic membrane, a series of three small bones in proximity to the ear drum where the ear drum and three bones are located in the inner ear, a cochlea and plural auditory nerves leading to the brain. In operation, sound waves enter the ear through the pinna where pressure differences between successive compressions and rarefactions set the eardrum vibrating. These vibrations pass to the cochlea where they are converted into electric signals. Finally, such signals travel along the auditory nerves to the brain, and the sound is heard.

A more detail discussion of one exemplary embodiment of the present invention: The magnetic field modulation system 18 has a transmitting coil 15 loosely coupled to a receiving coil 16, as shown in FIG. 2. The transmitting coil 15 and receiving coil 16 may, if desired, be fabricated by any convenient means known in the art so that radio frequency (RF) operation is allowed. The transmitting coil 15 and receiving coil 16 may, if desired, have any convenient form factor i.e., the shape of the transmitting coil 15 or receiving coil 16 may assume any suitable convenient geometric shape.

Figure 3:
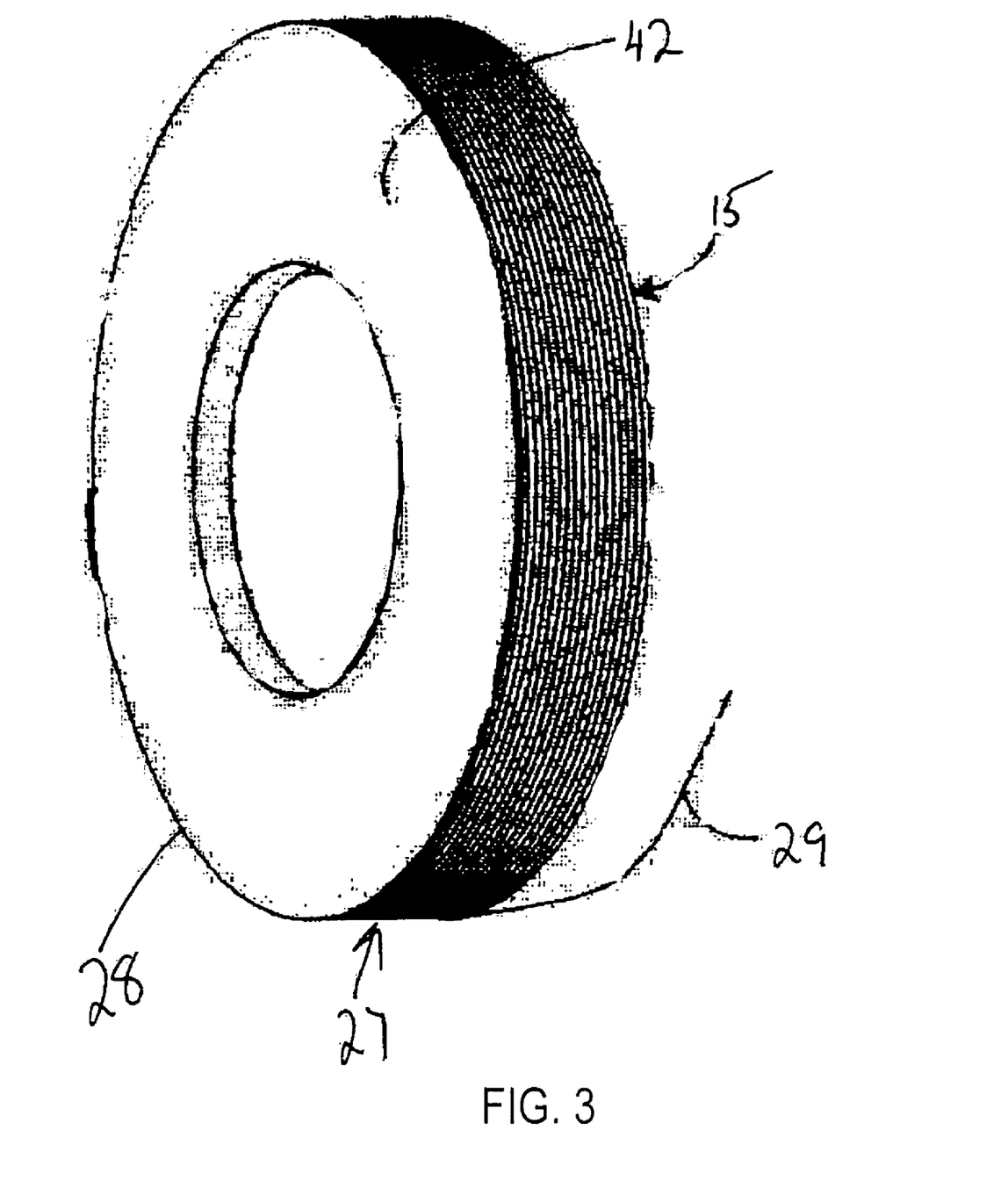

The transmitting coil 15 is positioned in the auditory canal 2, as shown in FIG. 1, adjacently spaced from the tympanic membrane or eardrum 22. The transmitting coil 15, as shown in FIG. 3, is electrically connected to the audio signal processor 14 via connecting wires 28 and 29. The receiving coil 16 is surgically implanted within the inner ear, as shown in FIG. 1, with the electrode 17 descending into the cochlea.

The transmitting coil 15, as shown in FIG. 3, may, if desired, be continuously wound about an air core with about 100 to 500 turns (see 27, FIG. 3) of, for example, 30 to 60 AWG bondable, solderable, copper magnet wire. Other configurations, turns and wire construction known to those skilled in the art are contemplated as being within the scope of the present invention. The bond coating on the wire may, if desired, be activated by a jet of heated air or chemically activated, as it is being wound or later baked. The finished transmitting coil 15 may, if desired, be about 1.0 mm thick by 3.0 mm to 4.0 mm in diameter and the diameter of the inner air core is about of 0.25 to 2.0 mm, and being understood that other dimensions are possible. Other configurations, turns and wire construction known to those skilled in the art are contemplated as being within the scope of the present invention. The bond coating sets when the transmitting coil 15 cools and holds its shape.

The coils exact shape, actual number of turns 27, as shown in FIG. 3, gauge and alloy makeup of the magnet wire are selected to have much lower inductive reactance than is normally connected to a class-D type switching amplifier. This allows the transmitting coil to operate in lock step with the output of the switching amplifier instead of averaging its signals. The transmit coil 15 creates an alternating electromagnetic field at a high, fixed frequency, which couples its energy to the receiver coil as shown in FIG. 4.

The receiving coil 16, may, if desired, be continuously wound about an air core with about 1500 to 3000 turns (see 31, FIG. 4) of, for example, 40 to 60 AWG bondable, solderable, copper magnet wire. Other configurations, turns and wire construction known to those skilled in the art are contemplated as being within the scope of the present invention. Optimally, the winding may, if desired, be 2274 turns of 50 AWG bondable, solderable, copper magnet wire. The bond coating on the wire may, if desired, be activated by a jet of heated air as it is being wound, chemically activated with acetone or baked after winding. The finished receiving coil 16 may, if desired, be about 1.0 mm thick by 3.0 mm to 4.0 mm in diameter and the diameter of the inner air core is about of 0.5 mm to 1.5 mm and being understood that other dimensions are possible. The bond coating sets when the receiving coil 16 cools and holds its shape. The receiving coil 16 may, if desired, be encased in a hermetically sealed titanium or other enclosure 26, as shown FIG. 2, to prevent damage or corrosion of the coil 31, capacitor 32 and connection to electrode 34.

Figure 4:
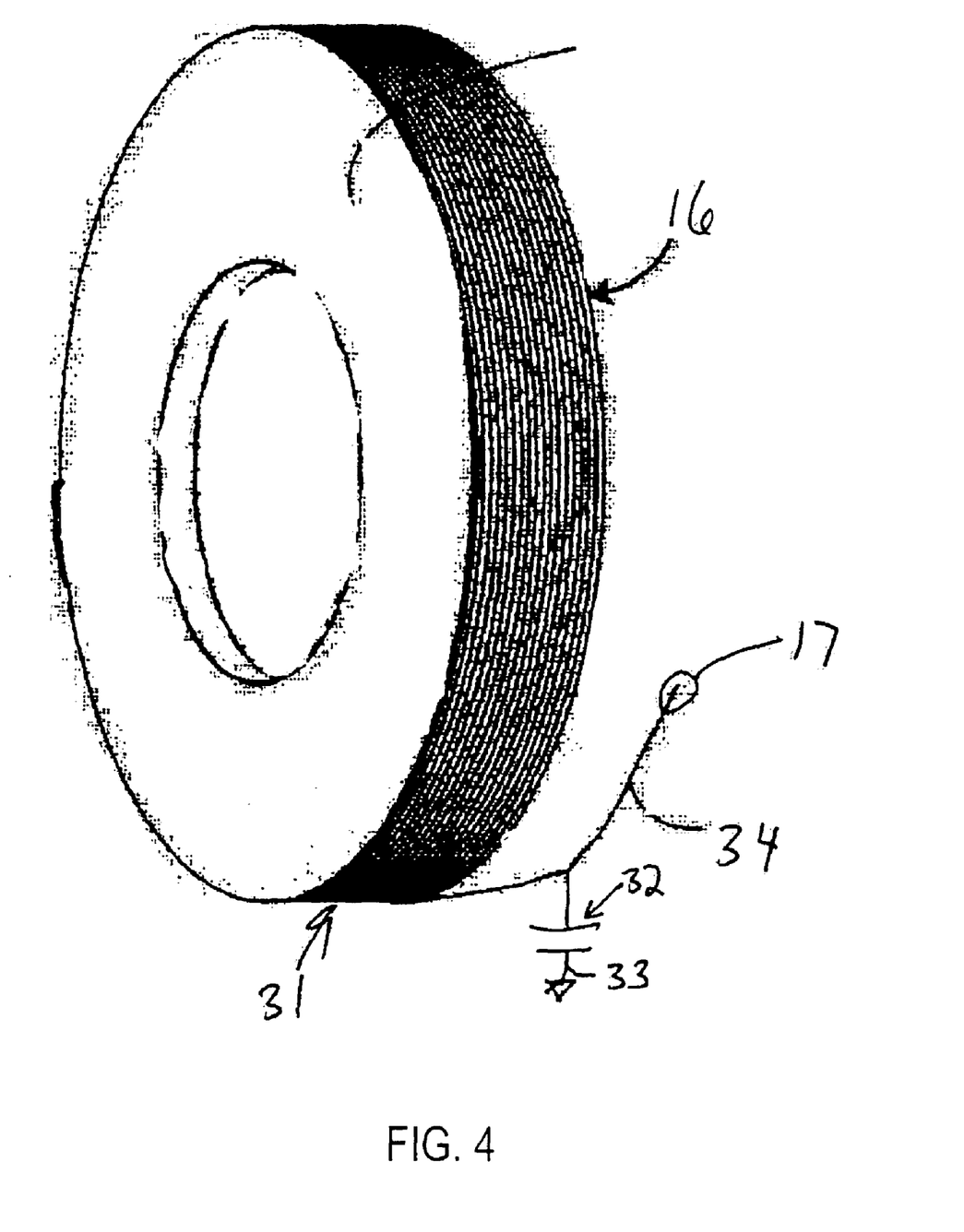
FIG. 4 illustrates a perspective of the receiving coil of the exemplary embodiment of FIG. 1.

The receiving coil 16, as shown in FIG. 4 has a pair of output wires 33 and 34 wherein the electrode 17 is electrically connected to output wire 33. The other output wire 34 may, if desired, be used for an electrical ground connection for the receiving coil 16 or attach to the inside of the case 26 allowing the outside of the case and attached support structures to become the electrical ground. A capacitor 32 may, if desired, be electrically connected across the output wires 33 and 34. The capacitor 32 is selected to match the inductance of the receiving coil 16 to aid in the demodulation of the 2 MHz modulated auditory signal received from the transmitting coil 15. For example, but not as a limitation, the inductance of the receiving coil's 16 windings generated from 2274 turns of 50 AWG copper magnet wire would receive a 15,000 pF (Pico-Farad) capacitor to demodulation of the encoded audio signal received from the transmitting coil 15.

The transmitting coil 15 and the receiving coil 16, may, if desired, be axially aligned on either side of the eardrum 20 with a working gap 34 spacing of about 1 mm to about 7 mm, though other distances may be achieved. The working gap 34 is derived empirically from the spacing between the transmitting coil 15, the receiving coil 16 and the outside diameter of the transmitting coil 15. The larger the outside diameter of the transmitting coil 15 (with the thickness of the coil remaining constant) the greater the distance between the transmitting coil 15 and the receiving coil 16. For example, a transmitting coil 15 having an outside diameter of 2 mm is spaced 3 mm from the receiving coil 16. The same signal level can be achieved using a larger 3 mm transmitting coil with spacing between the coils increased to 3 mm.

The receiving coil 16 may, if desired, be angularly positioned with respect to the transmitting coil 15. The angular position may, if desired, be from 0° to about 90° (degrees) without sufficient loss or degradation of the auditory signal received from the transmitting coil 15. The transmitting coil 15 and the receiving coil 16 may, if desired, be axially misaligned in the range of about 0.0 mm to about 4 mm without sufficient loss or degradation of the audio signal.

Figure 5:
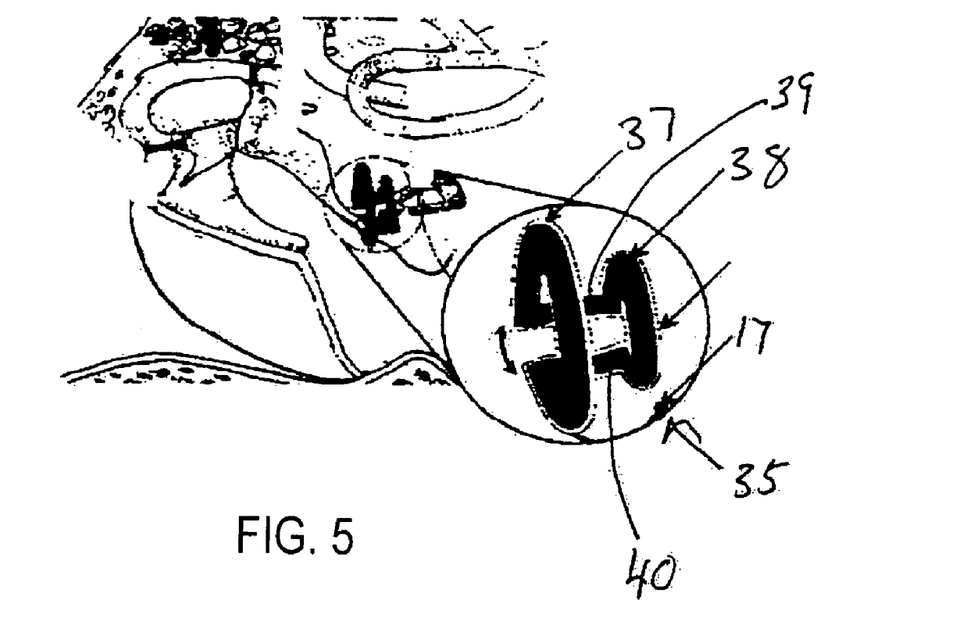
FIG. 5 illustrates a schematic diagram of a C-shaped receiving coil of the exemplary embodiment of FIG. 1.

One exemplary alternative form of the receiving coil 16, as shown in FIG. 5, is a flexible split coil comprising two C-shaped lobes 37 and 38. The C-shaped lobes 37 and 38 are spaced apart and aligned in the same plane. The C-shaped lobe 37 is larger than the C-shaped lobe 38 thereby allowing the receiving coil 16 to be adjacently spaced from the transmitting coil 15. The C-shaped lobe 38 receives only a very weak signal from the transmitting coil 15, so receiver signal cancellation is minimized in the reversing C-shaped lobe 38. A pair of transfer bridges 39 and 40 connect the C-shaped lobes 37 and 38 together. The transfer bridges 39 and 40 are spaced to enable the receiving coil 16 to have an opening along one side. This opening is sized to allow a surgeon to place the receiving coil 16 along the incus stapedial joint without separating the joint. The receiving coil 16 may then be clamped closed using a vascular clamp to prevent over tightening around the ossicles.

The receiving coil 16, as shown in FIG. 5, may, if desired, be sufficiently flexible permitting movement of the receiving coil 16 and enabling the transfer bridges 39 and 40 to remain closed around the incus stapedial joint once clamped during implantation. A UV curable bonding agent may, if desired, be coated onto the silicon-coated wire used to form the receiving coil 16. Subsequent to the forming of receiving coil 16 with the UV curing bonding agent and implantation about the ossicles, it is exposed to ultraviolet light for about 30 seconds. This exposure hardens the bonding agent on the wire, fixing the receiving coil 16 into position.

Figure 6:
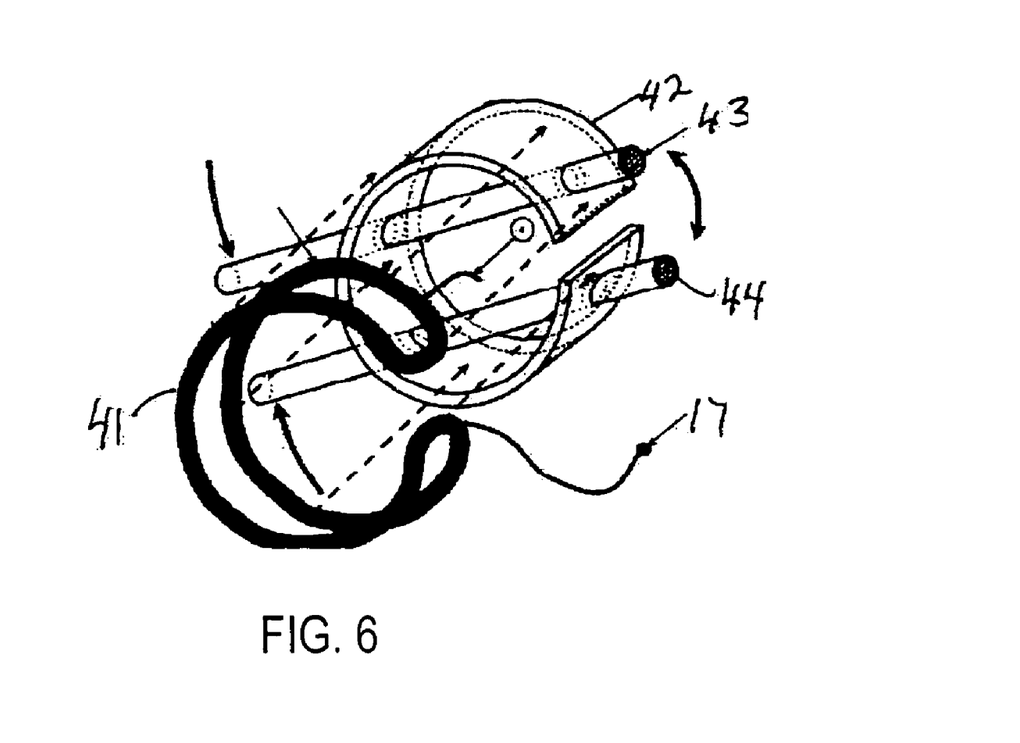
FIG. 6 illustrates a schematic diagram of a dual lobe C-shaped receiving coil of the exemplary embodiment of FIG. 1.

Another exemplary alternative embodiment of the receiving coil 16, as shown in FIG. 6 is a dual lobe receiving coil 41 and a split coil closing mechanism 42. The closing mechanism may, if desired, be fabricated from any suitable convenient material. For example, closing mechanism 42 may, if desired, be fabricated from a material having a memory to return to a preset shape after being deformed, compressed or contracted, such as, but not limited to, plastic, polymeric (e.g., shape memory polymer) ceramic, combination thereof, or the like.

The closing mechanism 42, as shown in FIG. 6, is inserted over the dual lobe receiving coil 41. This configuration enables a surgeon to open the dual lobe receiving coil 41 for insertion and then insert at least one rod 43 or 44 to close around the incus-stapedial joint. The center hub of the closing mechanism 42 provides the spring force to maintain the form of the dual lobe receiving coil 41. The rods 43 and 44, once in place, serve as an electrical return for the dual lobe receiving coil 41. The rods 43 and 44 may, if desired, be fabricated from any convenient material such as, but not limited to polymer, polymer derivative or polymer embedded metal, silver, gold, titanium, anodized metal and the like.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims, means-plus-function clause is intended to cover the structures described herein as performing the recited function and not only structural equivalents but also equivalent structures. Thus, by way of analogy, although a nail and a screw may not be structural equivalents in that a nail employs a cylindrical surface to secure wooden parts together whereas a screw employs a helical surface, in the environment of fastening wooden parts, a nail and a screw may be equivalent structures.

The invention claimed is:

1. A hearing aid for use in a human ear, the ear consisting in part of an auditory canal and a middle ear space and having a tympanic membrane disposed therebetween, the hearing aid comprising:
   an external portion to be inserted into the auditory canal, the external portion comprising:
      at least one microphone to receive sounds and convert the received sounds into electrical sound signals;
      an audio signal processor responsive to the electrical sound signals to provide processed electrical sound signals;
   a Class D switching amplifier responsive to the processed electrical sound signals to provide a switched electrical sound signal, the switching amplifier having a switching frequency;
   a transmitting coil to be positioned in said auditory canal adjacently spaced from said tympanic membrane, and connected to the switching amplifier to receive the switched electrical sound signal, the transmitting coil having a low inductance at the switching frequency; and
   a cochlear implant portion surgically implantable into the middle ear space, the cochlear implant comprising:
   a receiving coil electromagnetically coupled to the transmitting coil to receive the switched electrical sound signal and to provide a coupled switched electrical sound signal, the receiving coil to be positioned in the middle ear adjacently spaced from the tympanic membrane; and
   first and second electrodes connected to the receiving coil, the first electrode to be inserted into the cochlea to provide substantially the coupled switched electrical sound signal to the cochlea, and the second electrode to provide a signal return path for the coupled switched electrical sound signal.

2. The hearing aid of claim 1, wherein said transmitting coil is matched to the switching amplifier such that the transmitting coil operates in synchronization with the switching frequency of the switching amplifier.

3. The hearing aid of claim 1, wherein the switching amplifier has an output and said transmitting coil is coupled directly to the amplifier output.

4. The hearing aid of claim 1, wherein said transmitting coil's position is axially aligned with the position of said receiving coil.

5. The hearing aid of claim 1, wherein said receiving coil's position is angularly disposed to said transmitting coil's position.

6. The hearing aid of claim 1, wherein the spacing between said transmitting coil and said receiving coil is from about 1 mm to about 7 mm.

7. The hearing aid of claim 1 wherein the receiving coil has a thickness of approximately 1 millimeter.

8. The hearing aid of claim 1 wherein the receiving coil has a diameter of approximately 3 to 4 millimeters.

9. The hearing aid of claim 1, wherein the cochlear implant portion further comprises a capacitor functionally connected to said receiving coil to perform at least one of to match the inductance of the receiving coil to the switching frequency or to demodulate the coupled switched electrical sound signal to be provided to the cochlea.

10. The hearing aid of claim 1 wherein the transmitting coil has a thickness of approximately 1 millimeter.

11. The hearing aid of claim 1 wherein the switching amplifier has a switching frequency of approximately 2 MegaHertz.

12. The hearing aid of claim 1 wherein the transmitting coil and the receiving coil together act as a transformer with a low inductive impedance at the switching frequency.

13. The hearing aid of claim 1 wherein the transmitting coil comprises a plurality of turns of 30 to 60 AWG wire.

14. The hearing aid of claim 1 wherein the transmitting coil comprises 100 to 500 turns of 30 to 60 AWG wire.

15. The hearing aid of claim 1 wherein the receiving coil comprises a plurality of tunis of 40 to 60 AWG wire.

16. The hearing aid of claim 1 wherein the receiving coil comprises 1500 to 3000 turns of 40 to 60 AWG wire.

17. The hearing aid of claim 1 wherein said transmitting coil has a constant thickness and a diameter derived from the space separating said receiving coil and said transmitting coil.

18. The hearing aid of claim 1 wherein the transmitting coil has a diameter of approximately 3 to 4 millimeters.

19. A magnetic field modulation system for a cochlear implant surgically implantable into a human ear, the ear consisting in part of an auditory canal, the auditory canal having inserted therein an audio signal processor, switching amplifier and at least one microphone for receiving and processing auditory signals and a middle ear space having a tympanic membrane disposed therebetween, the magnetic field modulation system comprising:
   a) a transmitting coil to be positioned in said auditory canal adjacently space from said tympanic membrane:
   b) a receiving coil to be positioned in the middle ear adjacently spaced from the tympanic membrane;
   c) said transmitting coil having a constant thickness and a diameter derived from the space separating said receiving coil and said transmitting coil;
   d) said transmitting coil receiving auditory signals from said switching amplifier, said transmitting coil electromagnetically coupling said received audio signals to said receiving coil; and e) means connected to said receiving coil for demodulating and transmitting said electromagnetically coupled audio signals to the cochlea;

wherein said receiving coil comprises:

b1) a first C-shaped coil;

b2) a second C-shaped coil juxtaposition said first C-shaped coil;

b3) a pair of spaced apart transfer bridges connectively disposed to said first and said second C-shaped coil's open end points; and b4) means for operationally connecting said transfer bridges together thereby securing said receiving coil within the confines of the middle ear.

20. A magnetic field modulation system for a cochlear implant surgically implantable into a human ear, the ear consisting in part of an auditory canal, the auditory canal having inserted therein an audio signal processor, switching amplifier and at least one microphone for receiving and processing auditory signals and a middle ear space having a tympanic membrane disposed therebetween, the magnetic field modulation system comprising:

a) a transmitting coil to be positioned in said auditory canal adjacently spaced from said tympanic membrane;

b) a receiving coil to be positioned in the middle ear adjacently spaced from the tympanic membrane;

c) said transmitting coil having a constant thickness and a diameter derived from the space separating said receiving coil and said transmitting coil;

d) said transmitting coil receiving auditory signals from said switching amplifier, said transmitting coil electromagnetically coupling said received audio signals to said receiving coil; and e) means connected to said receiving coil for demodulating and transmitting said electromagnetically coupled audio signals to the cochlea;

wherein said receiving coil comprises:

b1) a C-shaped hub;

b2) a C-shaped dual lobe receiving coil;

b3) said C-shaped dual lobe receiving coil being slidably insertable into said C-shaped hub; and b4) means for operationally securing said C-shaped hub and C-shaped dual lobe receiving coil thereby securing said receiving coil within the confines of the middle ear.

21. A hearing aid external portion for use in a human ear and for use with a cochlear implant portion, the ear consisting in part of an auditory canal and a middle ear space and having a tympanic membrane disposed therebetween, the hearing aid external portion to be inserted into the auditory canal, the cochlear implant portion being surgically implantable into the middle ear space and having a receiving coil, the hearing aid external portion comprising:

at least one microphone to receive sounds and convert the received sounds into electrical sound signals;

an audio signal processor responsive to the electrical sound signals to provide processed electrical sound signals;

a Class D switching amplifier responsive to the processed electrical sound signals to provide a switched electrical sound signal, the switching amplifier having a switching frequency; and a transmitting coil to be positioned in said auditory canal adjacently spaced from said tympanic membrane, and connected to the switching amplifier to receive the switched electrical sound signal, the transmitting coil having a low inductance at the switching frequency, the transmitting coil to be electromagnetically coupled to the receiving coil.

22. The hearing aid of claim 21, wherein said transmitting coil is matched to the switching amplifier such that the transmitting coil operates in synchronization with the switching frequency of the switching amplifier.

23. The hearing aid external portion of claim 21 wherein the switching amplifier has a switching frequency of approximately 2 MegaHertz.

24. The hearing aid external portion of claim 21 wherein the transmitting coil has a thickness of approximately 1 millimeter.

25. The hearing aid external portion of claim 21 wherein the transmitting coil has a diameter of approximately 3 to 4 millimeters.

* * * * *